United States Patent
Chiu et al.

(10) Patent No.: US 9,540,296 B2
(45) Date of Patent: Jan. 10, 2017

(54) PROCESS FOR DRYING HCFO-1233ZD

(71) Applicant: Honeywell International Inc., Morris Plains, NJ (US)

(72) Inventors: Yuon Chiu, Denville, NJ (US); Stephen A. Cottrell, Baton Rouge, LA (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/046,591

(22) Filed: Feb. 18, 2016

(65) Prior Publication Data
US 2016/0272560 A1    Sep. 22, 2016

Related U.S. Application Data

(60) Provisional application No. 62/135,282, filed on Mar. 19, 2015.

(51) Int. Cl.
 *C07C 17/38* (2006.01)
 *C07C 17/389* (2006.01)
(52) U.S. Cl.
 CPC .................. *C07C 17/389* (2013.01)
(58) Field of Classification Search
 CPC .......... C07C 17/10; C07C 17/04; C07C 17/38; C07C 17/389
 USPC .................................. 570/177, 179
 See application file for complete search history.

(56) References Cited

U.S. PATENT DOCUMENTS

| | | | |
|---|---|---|---|
| 6,059,860 A * | 5/2000 | Larson | B01D 53/02 55/512 |
| 7,084,315 B2 | 8/2006 | Corr et al. | |
| 8,067,650 B2 | 11/2011 | Wang et al. | |
| 8,212,092 B2 | 7/2012 | Rao et al. | |
| 8,921,621 B2 | 12/2014 | Cottrell et al. | |
| 2010/0162738 A1 | 7/2010 | Low et al. | |
| 2011/0105809 A1 | 5/2011 | Devic et al. | |
| 2011/0172472 A1 * | 7/2011 | Sakyu | C07C 17/20 570/160 |
| 2012/0266750 A1 | 10/2012 | Thomas et al. | |
| 2012/0296127 A1 | 11/2012 | Cottrell et al. | |
| 2013/0158305 A1 | 6/2013 | Takahashi | |
| 2014/0275662 A1 | 9/2014 | Kopkalli et al. | |
| 2014/0357907 A1 * | 12/2014 | Okamoto | C07C 17/10 570/153 |
| 2015/0099907 A1 * | 4/2015 | Imura | C07C 17/358 570/151 |

FOREIGN PATENT DOCUMENTS

EP      2778151 A1    9/2014

OTHER PUBLICATIONS

PCT/US2016/021218 International Search Report & Written Opinion—Jun. 1, 2016.

* cited by examiner

*Primary Examiner* — Jafar Parsa
(74) *Attorney, Agent, or Firm* — Bruce O. Bradford

(57) ABSTRACT

Disclosed is a process to dry 1-chloro-3,3,3-trifluoropropene (HCFO-1233zd) or its mixtures by washing with water and or alkaline solution. The resulting liquid mixture, containing HCFO-1233zd, other organic, and water, is allowed to settle, and thereafter, the lighter water layer is decanted off from the top of the mixture. The heavier HCFO-1233zd layer is then withdrawn from the bottom of the decanter to a desiccant dryer (e.g., molecular sieve, activated alumina, silica gel, and the like) to further remove the residual soluble moisture from the HCFO-1233zd to about 80 ppm or less.

11 Claims, No Drawings

9,540,296 B2

PROCESS FOR DRYING HCFO-1233ZD

CROSS REFERENCE TO RELATED APPLICATIONS

This application claims domestic priority from commonly owned copending U.S. Provisional Patent Application Ser. No. 62/135,282, filed Mar. 19, 2015, the disclosure of which is hereby incorporated herein by reference in its entirety.

FIELD OF THE INVENTION

In the commercial production of 1-chloro-3,3,3-trifluoropropene (HCFO-1233zd) the crude product from the process will require aqueous washing to remove HF, HCl, and other acidic components. The present invention provides a novel method to economically dry and recover the HFO-1233zd.

BACKGROUND OF THE INVENTION

Commercial uses for HCFO-1233zd (1233zd) include foam blowing agent and solvent applications. In such applications, tight control of moisture content is typically needed to meet customer requirements. Occasionally, due to process issues, the moisture level in 1233zd may exceed specification limits.

Various 1233zd production processes have been disclosed. One example is shown in U.S. Pat. No. 8,921,621, which disclosed a process for the production of HCFO-1233zd comprising the steps of: (a) reacting HCC-240 and HF in a high pressure liquid phase reactor, with subsequent steps including step (h) of "feeding the overhead crude HCFO-1233zd stream to a caustic scrubber to remove any remaining acidity and drying the scrubbed stream with a drying agent . . . ".

In the '621 process, one objective is to provide enough drying agent to remove the water in the process stream, and one must be prepared that the overhead crude HCFO-1233zd vapor stream could be fully saturated with water. In such a case, it is estimated that for every 1,000 pounds of HCFO-1233zd vapor produced, one could need to remove at least 4 pounds of water. Accordingly, if using a typical molecular sieve desiccant, which can adsorb up to about 15 wt % moisture, one would need to use up to about 27 pounds of molecular sieve for every 1,000 pounds of HCFO-1233zd generated in the process. This invention is designed to significantly reduce the desiccant consumption required for such a process.

SUMMARY OF THE INVENTION

In one embodiment of the present invention, crude HCFO-1233zd is first washed with water and/or an alkaline solution. The washed vapor is then condensed. The condensed mixture, containing HCFO-1233zd, other organics, and water, is then settled and the lighter water layer is decanted off. The heavier HCFO-1233zd and other organic layer is then withdrawn from the bottom of the decanter to a desiccant dryer (containing e.g., molecular sieve, activated alumina, silica gel, $CaSO_4$, mixtures thereof, and the like) to further remove residual soluble moisture present in the HCFO-1233zd. After treatment in the desiccant dryer the moisture content is as low as, or lower than, about 80 ppm, preferably as low as, or lower than, about 50 ppm, more preferably as low as, or lower than, about 20 ppm, and most preferably as low as, or lower than, about 10 ppm.

It should be appreciated by those persons having ordinary skill in the art(s) to which the present invention relates that any of the features described herein in respect of any particular embodiment and/or embodiment of the present invention can be combined with one or more of any of the other features of any other embodiments and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

As described above, U.S. Pat. No. 8,921,621 describes a process for the production of 1-chloro-3,3,3-trifluoropropene (HCFC-1233zd) on a commercial scale from the reaction of 1,1,1,3,3-pentachloropropane (HCC-240fa) and HF.

In one embodiment of the '621 process, HCC-240fa and HF are fed to a liquid phase reactor operating at high pressure. The resulting product stream consisting of 1233zd, HCl, HF, and other byproducts is partially condensed to recover HF by phase separation. The recovered HF phase is recycled to the reactor. The HCl is scrubbed from the vapor stream and recovered as an aqueous solution. The remaining organic components including the desired HCFC-1233zd are scrubbed, dried and distilled to meet commercial product specifications.

In the present invention, wet and acid-free 1233zd (HCFO-1233zd) crude vapor from the caustic scrubber outlet is condensed in a condenser. The condensed wet 1233zd will then flow into a distillation pump tank, where the water will settle as the top layer and the 1233zd will settle as bottom layer. At a production rate of 1000 to 1500 lb/hr of 1233zd, including scrubber liquid entrainment, it is expected that about 2 gals/hr of free water will accumulate in the distillation pump tank (capacity of 19,000 gallons). Accordingly, it is estimated that the tank can easily handle about 4,000 gal of free water, at least temporarily.

During commercial processing of 1233zd, it is expected that one should not need to attend to this water for up to 3 months at 1,500 lb/hr crude 1233zd production rate. A monitoring program to track this water volume, and its acidity content, e.g., to prevent any corrosion or overspill incident, has been developed. The water is expected to contain about 2,000 PPM crude 1233zd, or about 0.03 lb/hr organic. This water can be recycled to the caustic scrubber for organic recovery and disposal.

EXAMPLE 1

Processing of 1,000 lbs of Crude HCFO-1233zd.

1,000 lbs of wet and acid-free crude HCFO-1233zd vapor from the caustic scrubber outlet is condensed in a condenser. The condensed wet HCFO-1233zd will then flow into a decanter. The water will settle as top layer while the HCFO-1233zd will settle as bottom layer.

The top water layer is withdrawn and expected to have about 4 lbs of water and to contain about 2,000 PPM of dissolved HCFO-1233zd or 0.008 lbs. This water can be recycled to the caustic scrubber for organic recovery or be disposed.

The bottom HCFO-1233zd organic layer is withdrawn and expected to have about 1,000 lbs of HCFO-1233zd and to contain about 400 PPM of dissolved water or 0.4 lbs. This resulting HCFO-1233zd stream is then dried with a drying agent such as molecular sieve 3A or 4A, activated alumina, silica gel, $CaSO_4$, and the like.

Using a commercial 3A molecular sieve desiccant which can adsorb up to 15% moisture, this improved process would have consumed only 2.7 pounds of molecular sieve for every 1,000 pounds of HCFO-1233zd processed. The water content is about 10 ppm after this treatment.

In view of this low desiccant consumption rate, the drying equipment size can be made much smaller than those used in prior art processing. Furthermore, given that the molecular sieve can be regenerated, the ultimate drying agent consumption can be minimized.

EXAMPLE 2

Processing 1,000 lbs of Crude HCFO-1233zd.

1,000 lbs of liquid crude HCFO-1233zd containing 10 lbs of HF acid is mixed with about 300 lbs of water and/or diluted caustic solution and then washed to remove the acid at sub-cooled temperature while maintaining the mixture in a liquid phase. The resulting wet and acid free HCFO-1233zd will then flow into a decanter. The water or caustic solution will settle as top layer while the HCFO-1233zd will settle as bottom layer. The above can be carried out stage-wise (e.g., first washing with water and decanting, then followed by washing with aqueous caustic and decanting, etc.).

The top water or caustic layer is withdrawn and expected to have about 300 lbs of water and to contain about 2,000 PPM of dissolved HCFO-1233zd or 0.6 lbs. This water or caustic solution can subsequently be heated or stripped to recover valuable organic or be disposed.

The bottom HCFO-1233zd organic layer is withdrawn and expected to have about 1,000 lbs of HCFO-1233zd and to contain about 400 PPM of dissolved water or 0.4 lbs. This resulting HCFO-1233zd stream is then dried with a drying agent such as molecular sieve 3A or 4A, activated alumina, silica gel, $CaSO_4$, and the like.

Using a commercial 3A molecular sieve desiccant which can adsorb up to 15% moisture, this improved process would have consumed only 2.7 pounds of mole sieve for every 1,000 pounds of HCFO-1233zd processed. The water content is about 10 ppm after this treatment.

In view of this low desiccant consumption rate, the drying equipment size can be made much smaller than those used in prior art processing. Furthermore, given that the molecular sieve can be regenerated, the ultimate drying agent consumption can be minimized.

EXAMPLE 3

Processing of Crude 1233zd in a Pilot Plant 100 lbs of wet and acid-free crude HCFO-1233zd vapor from the caustic scrubber outlet is condensed in a condenser. The condensed wet HCFO-1233zd will then flow into a decanter. The water will settle as top layer while the HCFO-1233zd will settle as bottom layer.

The top water layer is withdrawn and discarded

The bottom HCFO-1233zd organic layer is withdrawn. This resulting HCFO-1233zd stream is then dried with a drying agent such as molecular sieve 3A or 4A, activated alumina, silica gel, $CaSO_4$, and the like.

Using a commercial 3A molecular sieve desiccant which can adsorb up to 15% moisture, this improved process would have consumed only 2.7 pounds of molecular sieve for every 1,000 pounds of HCFO-1233zd processed. The water content is about 10 ppm after this treatment.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. In the process of purifying crude 1-chloro-3,3,3-trifluoropropene (HCFO-1233zd), wherein the crude HCFO-1233zd product requires aqueous washing to remove HF, HCl, and other acidic components,
   the improvement comprising conducting each of the following steps in order:
   (a) washing the crude HCFO-1233zd with water to form a washed mixture;
   (b) condensing the washed mixture; and
   (c) separating the washed mixture into a lighter water layer and heavier HCFO-1233zd layer, followed by drying the HCFO-1233zd layer with a desiccant, thereby producing an HCFO-1233zd product with a moisture level of 80 ppm or less.

2. The process of claim 1, wherein the moisture level is about 50 ppm or less.

3. The process of claim 1, wherein the moisture level is about 20 ppm or less.

4. The process of claim 1, wherein the moisture level is about 10 ppm or less.

5. The process of claim 1, wherein the crude HFC-1233zd is washed with an alkaline solution.

6. The process of claim 1, wherein the desiccant is selected from the group consisting of molecular sieve 3A, 4A, activated alumina, silica gel, $CaSO_4$, and mixtures thereof.

7. The process of claim 6, wherein the desiccant comprises molecular sieve 3A.

8. The process of claim 6, wherein the desiccant is comprises molecular sieve 4A.

9. The process of claim 6, wherein the desiccant comprises activated alumina.

10. The process of claim 6, wherein the desiccant comprises silica gel.

11. The process of claim 6, wherein the desiccant comprises $CaSO_4$.

* * * * *